United States Patent
Joung et al.

(10) Patent No.: US 11,725,228 B2
(45) Date of Patent: Aug. 15, 2023

(54) METHODS FOR DETECTING SITE-SPECIFIC AND SPURIOUS GENOMIC DEAMINATION INDUCED BY BASE EDITING TECHNOLOGIES

(71) Applicant: The General Hospital Corporation, Boston, MA (US)

(72) Inventors: J. Keith Joung, Winchester, MA (US); James Angstman, Charlestown, MA (US); Jason Michael Gehrke, Cambridge, MA (US)

(73) Assignee: The General Hospital Corporation, Boston, MA (US)

(*) Notice: Subject to any disclaimer, the term of this patent is extended or adjusted under 35 U.S.C. 154(b) by 268 days.

(21) Appl. No.: 16/754,648

(22) PCT Filed: Oct. 11, 2018

(86) PCT No.: PCT/US2018/055406
§ 371 (c)(1),
(2) Date: Apr. 8, 2020

(87) PCT Pub. No.: WO2019/075197
PCT Pub. Date: Apr. 18, 2019

(65) Prior Publication Data
US 2020/0239930 A1    Jul. 30, 2020

Related U.S. Application Data

(60) Provisional application No. 62/571,222, filed on Oct. 11, 2017.

(51) Int. Cl.
*C12Q 1/44* (2006.01)
*C12Q 1/6855* (2018.01)
*C12Q 1/6869* (2018.01)

(52) U.S. Cl.
CPC ............ *C12Q 1/44* (2013.01); *C12Q 1/6855* (2013.01); *C12Q 1/6869* (2013.01); *C12Q 2521/301* (2013.01); *C12Q 2523/301* (2013.01); *C12Q 2525/191* (2013.01); *C12Q 2531/113* (2013.01)

(58) Field of Classification Search
CPC ...... C12Q 1/44; C12Q 1/6855; C12Q 1/6869; C12Q 2521/301; C12Q 2523/301; C12Q 2525/191; C12Q 2531/113
See application file for complete search history.

(56) References Cited

U.S. PATENT DOCUMENTS

| | | | |
|---|---|---|---|
| 7,803,550 B2 | 9/2010 | Makarov et al. | |
| 8,071,312 B2 | 12/2011 | Makarov et al. | |
| 8,399,199 B2 | 3/2013 | Makarov et al. | |
| 8,420,319 B2 | 4/2013 | Mikawa | |
| 8,697,359 B1 | 4/2014 | Zhang | |
| 8,728,737 B2 | 5/2014 | Makarov et al. | |
| 9,163,284 B2 | 10/2015 | Iliu et al. | |
| 9,322,006 B2 | 4/2016 | Liu et al. | |
| 9,512,446 B1 | 12/2016 | Joung et al. | |
| 9,822,407 B2 | 11/2017 | Joung et al. | |
| 9,850,484 B2 | 12/2017 | Joung et al. | |
| 9,988,674 B2 | 6/2018 | Joung et al. | |
| 10,233,490 B2 | 3/2019 | Stapleton et al. | |
| 10,501,794 B2 | 12/2019 | Joung et al. | |
| 11,028,429 B2 | 6/2021 | Joung et al. | |
| 2005/0202490 A1 | 9/2005 | Makarov et al. | |
| 2005/0221341 A1 | 10/2005 | Shimkets et al. | |
| 2006/0040297 A1 | 2/2006 | Leamon et al. | |
| 2006/0292611 A1 | 12/2006 | Berka et al. | |
| 2009/0082295 A1 | 3/2009 | Jungneli et al. | |
| 2010/0076057 A1 | 3/2010 | Sontheimer et al. | |
| 2010/0317722 A1 | 12/2010 | Lavon | |
| 2011/0060493 A1 | 3/2011 | Miura et al. | |
| 2011/0189776 A1 | 8/2011 | Terns et al. | |
| 2011/0207221 A1 | 8/2011 | Cost et al. | |
| 2011/0223638 A1 | 9/2011 | Wiedenheft et al. | |
| 2011/0281736 A1 | 11/2011 | Drmanac et al. | |
| 2011/0287545 A1 | 11/2011 | Cost | |
| 2012/0157322 A1 | 6/2012 | Myllykangas et al. | |
| 2012/0208705 A1 | 8/2012 | Steemers et al. | |
| 2013/0130248 A1 | 5/2013 | Haurwitz et al. | |
| 2013/0137605 A1 | 5/2013 | Shendure et al. | |
| 2013/0143204 A1 | 6/2013 | Von Kalle | |
| 2013/0203605 A1 | 8/2013 | Shendure et al. | |
| 2013/0303461 A1 | 11/2013 | Iafrate et al. | |
| 2013/0309668 A1 | 11/2013 | Makarov et al. | |
| 2014/0024542 A1 | 1/2014 | Richards | |
| 2014/0170753 A1 | 6/2014 | Zhang | |
| 2014/0179006 A1 | 6/2014 | Zhang | |
| 2014/0179770 A1 | 6/2014 | Zhang et al. | |
| 2014/0186843 A1 | 7/2014 | Zhang et al. | |

(Continued)

FOREIGN PATENT DOCUMENTS

CN    102373288    3/2012
EP    3530737 A1    8/2019
(Continued)

OTHER PUBLICATIONS

AU Office Action in Australian Application No. 2015280069, dated Nov. 6, 2020, 6 pages.
CA Office Action in Canadian Appln. No. 2,953,362, dated Jun. 25, 2021, 5 pages.
CN Office Action in Chinese Appln. No. 201580045542, dated Jul. 14, 2020, 29 pages (with English translation).
CN Office Action in Chinese Appln. No. 201580045542.3, dated Feb. 1, 2021, 42 pages (with English translation).
CN Office Action in Chinese Appln. No. 201680065929.X, dated Jan. 29, 2021, 21 pages (with English translation).
EP Office action in European Appln. No. 16845183, dated Jun. 9, 2020, 7 pages.

(Continued)

*Primary Examiner* — David C Thomas
(74) *Attorney, Agent, or Firm* — Fish & Richardson P.C.

(57) ABSTRACT

Methodologies to detect off-target mutations induced by the deaminase activity of Base Editing technology.

11 Claims, 4 Drawing Sheets
Specification includes a Sequence Listing.

(56) References Cited

U.S. PATENT DOCUMENTS

| | | |
|---|---|---|
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0199767 A1 | 7/2014 | Barrangou et al. |
| 2014/0201857 A1 | 7/2014 | Fahrenkrug et al. |
| 2014/0212869 A1 | 7/2014 | Sampas et al. |
| 2014/0227787 A1 | 8/2014 | Zhang |
| 2014/0234289 A1 | 8/2014 | Liu et al. |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0242702 A1 | 8/2014 | Chen et al. |
| 2014/0248702 A1 | 9/2014 | Zhang et al. |
| 2014/0256046 A1 | 9/2014 | Zhang et al. |
| 2014/0271987 A1 | 9/2014 | Manomy et al. |
| 2014/0273230 A1 | 9/2014 | Chen et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |
| 2014/0294773 A1 | 10/2014 | Brouns et al. |
| 2014/0295556 A1 | 10/2014 | Joung et al. |
| 2014/0295557 A1 | 10/2014 | Joung et al. |
| 2014/0298547 A1 | 10/2014 | Sastry-Dent et al. |
| 2014/0304853 A1 | 10/2014 | Ainley et al. |
| 2014/0309487 A1 | 10/2014 | Lee et al. |
| 2014/0310828 A1 | 10/2014 | Lee et al. |
| 2014/0310830 A1 | 10/2014 | Zhang et al. |
| 2014/0315985 A1 | 10/2014 | May et al. |
| 2014/0335063 A1 | 11/2014 | Cannon et al. |
| 2014/0335620 A1 | 11/2014 | Zhang et al. |
| 2014/0349400 A1 | 11/2014 | Jakimo et al. |
| 2014/0357530 A1 | 12/2014 | Zhang et al. |
| 2014/0377868 A1 | 12/2014 | Joung et al. |
| 2015/0024500 A1 | 1/2015 | Yu et al. |
| 2015/0031134 A1 | 1/2015 | Zhang et al. |
| 2015/0045546 A1 | 2/2015 | Siksnys et al. |
| 2015/0050699 A1 | 2/2015 | Siksnys et al. |
| 2015/0044191 A1 | 5/2015 | Liu et al. |
| 2016/0304950 A1 | 10/2016 | Joung et al. |
| 2017/0073747 A1 | 3/2017 | Joung et al. |
| 2017/0088833 A1 | 3/2017 | Joung et al. |
| 2017/0198344 A1 | 7/2017 | Vaisvila et al. |
| 2017/0253909 A1* | 9/2017 | Uemori .................... C12N 9/22 |
| 2018/0073012 A1 | 3/2018 | Liu et al. |
| 2018/0087104 A1 | 3/2018 | Joung et al. |
| 2018/0245071 A1 | 8/2018 | Joung et al. |
| 2018/0265920 A1 | 9/2018 | Joung et al. |
| 2019/0177710 A1 | 6/2019 | Lee |
| 2020/0010889 A1 | 1/2020 | Joung et al. |
| 2020/0131536 A1 | 4/2020 | Kim |
| 2020/0199665 A1 | 6/2020 | Joung et al. |
| 2021/0071248 A1 | 3/2021 | Joung et al. |
| 2021/0155984 A1 | 5/2021 | Joung et al. |

FOREIGN PATENT DOCUMENTS

| | | |
|---|---|---|
| JP | 2009-502202 | 1/2009 |
| JP | 2013/518602 | 5/2013 |
| JP | 2013-544498 | 12/2013 |
| JP | 2014-506788 | 3/2014 |
| JP | 2015-521468 | 7/2015 |
| JP | 2018-530536 | 10/2018 |
| WO | WO 2008/108989 | 9/2008 |
| WO | WO 2010/054108 | 5/2010 |
| WO | WO 2011/086118 | 7/2011 |
| WO | WO 2011/100058 | 8/2011 |
| WO | WO 2012/065143 | 5/2012 |
| WO | WO 2012/164565 | 12/2012 |
| WO | WO 2013/078470 | 5/2013 |
| WO | WO 2013/098244 | 7/2013 |
| WO | WO 2013/176772 | 11/2013 |
| WO | WO 2013/191775 | 12/2013 |
| WO | WO 2014/008447 | 1/2014 |
| WO | WO 2014/018080 | 1/2014 |
| WO | WO 2014/071070 | 5/2014 |
| WO | WO 2014/071361 | 5/2014 |
| WO | WO 2014/093701 | 6/2014 |
| WO | WO 2015/074017 | 5/2015 |
| WO | WO 2015/117040 | 8/2015 |
| WO | WO 2015/200378 | 12/2015 |
| WO | WO 2016/081798 | 5/2016 |
| WO | WO 2016/141224 | 9/2016 |
| WO | WO 2017/040348 | 3/2017 |
| WO | WO 2017/059313 | 4/2017 |
| WO | WO 2017/079593 | 5/2017 |
| WO | WO 2017/218979 | 12/2017 |
| WO | WO 2018/052247 | 3/2018 |
| WO | WO 2018/218166 | 11/2018 |
| WO | WO 2018/218188 | 11/2018 |
| WO | WO 2019/075197 | 4/2019 |

OTHER PUBLICATIONS

EP Office Action in European Appln. No. 16852752.1, dated Nov. 3, 2020, 5 pages.

EP Partial Supplementary European Search Report in European Appln. No. 18867278.6, dated Jun. 15, 2021, 12 pages.

Hess et al., "Methods and Applications of CRISPR-Mediated Base Editing in Eukaryotic Genomes," Molecular Cell, 2017, 68:26-43.

IN Office Action in Indian Appln. No. 201617043121, dated Dec. 8, 2020, 6 pages.

JP Office Action in Japanese Appln. No. 2018-513347, dated Sep. 15, 2020, 11 pages (with English translation).

JP Office Action in Japanese Appln. No. 2018-516489, dated Jul. 21, 2020, 8 pages (with English translation).

Liang et al., "Off-target effects of cytidine base editor and adenine base editor: What can we do?," Journal of Genetics and Genomics, 2019, 46:509-512.

PCT International Preliminary Report on Patentability in International Appln. No. PCT/US2019/027788, dated Oct. 20, 2020, 16 pages.

Rees & Liu, "Base editing: precision chemistry on the genome and transcriptome of living cells," Nat. Rev. Genet., Dec. 2018, 19(12):770-788.

Malinin et al., "Defining genome-wide CRISPR-Cas genome-editing nuclease activity with Guide-seq," Nature Protocols, Dec. 2021, 16:5592-5615.

Shi et al., "Guide-Seq to detect genome-wide double-stranded breaks in plants," Cell Press, Oct. 2016, 21(10):815-818.

Wienert et al., "Unbiased detection of CRISPR off-targets in vivo using Discover-Seq," Science, Apr. 2019, 364(6437):286-289.

Akhtar et al., "Using TRIP for genome-wide position effect analysis in cultured cells," Nat. Protoc., May 2014, 9(6):1255-1281.

EP Extended Search Report in European Appln. No. 18867278.6, dated Sep. 15, 2021, 10 pages.

Al-Attar et al, "Clustered Regularly Interspaced Short Palindromic Repeats (CRISPRs): The Hallmark of an Ingenious Antiviral Defense Mechanism in Prokaryotes," Biol Chem. 2011, 392(4):277-289.

Anders et al, "Structural basis of PAM-dependent target DNA recognition by the Cas9 endonuclease," Nature, Jul. 2014, 513:569-573.

Aynaud et al., "Human Tribbles 3 protects nuclear DNA from cytidine deamination by APOBEC3A," Journal of Biological Chemistiy, Nov. 2012, 287(46):39182-39192.

Barrangou & May, "Unraveling the potential of CRISPR-Cas9 for gene therapy," Expert Opin. Biol. Ther., 2014, 15:311-314.

Belanger et al., "Deamination intensity profiling of human APOBEC3 protein activity along the near full-length genomes of HIV-1 and MoMLV by HyperHRM analysis," Virology, Jan. 2014, 448:168-175.

Berg et al., "Section 7.1. Homologs are Descended from a Common Ancestor," in Biochemistry, W.H. Freeman, pub. 2002, [retrieved on Jan. 30, 2017]. Retrieved from the Internet: URL <https://www.ncbi.nlm.nih.gov/books/NBK22355/>. 1 page.

Bikard et al, "Programmable repression and activation of bacterial gene expression using an engineered CRISPR-Cas system," Nucleic Acids Res., Aug. 2013, 41(15):7429-7437.

(56) References Cited

OTHER PUBLICATIONS

Bolukbasi et al., "Creating and evaluating accurate CRISPR-Cas9 scalpels for genomic surgery," Nat Meth, Jan. 2016, 13: 41-50.
Briggs et al., "Removal of deaminated cytosines and detection of in vivo methylation in ancient DNA," Nucleic Acids Research, Apr. 2010, 38(6):e87, 12 pages.
Cameron et al., "Mapping the genomic landscape of CRISPR-Cas9 cleavage," Nature Methods, 2017, 10 pages.
Canela et al., "DNA Breaks and End Resection Measured Genomewide by End Sequencing," Molecular Cell, 2016, 63: 1-14.
Canver et al, "BCL11A enhancer dissection by Cas9mediated in situ saturating mutagenesis," Nature, 2015, 527(7577):192-197.
Carroll, "A Crispr Approach to Gene Targeting," Molecular Therapy, Sep. 2012, 20:(9)1658-1660.
Casini et al, "A highly specific SpCas9 variant is identified by in vivo screening in yeast," Nat. Biotechnol., Mar. 2018, 36(3):265-271.
Cencic et al., "Protospacer Adjacent Motif (PAM)-Distal Sequences Engage CRISPR Cas9 DNA Target Cleavage," Oct. 2014, PLOS One, 9(10): e109213.
Chavez et al., "Highly-efficient Cas9-mediated transcriptional programming," Nat. Meth., Apr. 2015, 12(4):326-328.
Chen & Zhao, "A highly sensitive selection method for directed evolution of homing endonucleases," Nucleic Acids Res., Oct. 2005, 33, e154, 7 pages.
Chen et al., "Enhanced proofreading governs CRISPR-Cas9 targeting accuracy," Nature, Oct. 2017, 550(7676):407-410.
Cho et al., "Analysis of off-target effects of CRISPR/Case-derived RNA-guided endonucleases and nickases," Genome Res., 2014, 24:132-141.
Cho et al., "Targeted genome engineering in human cells with the Cas9 RNA-guided endonuclease," Nat Biotechnol., 2013, 31:230-232.
Choi & Meyerson, "Targeted genomic rearrangements using CRISPR/Cas technology," Nat Commun., Apr. 24, 2014, 5:3728, doi: 10.1038/ncomms4728.
Chylinski et al, "The tracrRNA and Cas9 families of type II CRISPR-Cas immunity systems," RNA Biol., May 2013, 10:726-737.
CN Office Action in Chinese Appln. No. 201580045542.3, dated Feb. 3, 2020, 19 pages, (with English translation).
CN Office Action in Chinese Appln. No. 201580045542.3, dated Jul. 22, 2019, 25 pages, (with English translation).
Cong et al., "Multiplex genome engineering using CRISPR/Cas systems," Science, 2013, 339:819-823 (Author Manuscript).
Courtney et al, "CRISPR/Cas9 DNA cleavage at SNP-derived PAM enables both in vitro and in vivo KRT12 mutation-specific targeting," Gene. Ther., Aug. 2015, 23(1):108-12.
Cox et al., "Therapeutic genome editing: prospects and challenges," Nat Med, 21: 121-131 (2015.
Cradick et al., "CRISPR/Cas9 systems targeting beta-globin and CCR5 genes have substantial off-target activity," Nucleic Acids Res., 2013, 41(20):9584-92.
Crosetto et al, "Nucleotide-resolution DNA double-strand break mapping by next-generation sequencing," Apr. 2013, Nat Methods 10(4): 361-365.
Deltcheva et al, "CRISPR RNA maturation by trans-encoded small RNA and host factor RNase III," Nature, Mar. 2011, 471(7340):602-607.
DiCarlo et al., "Genome engineering in *Saccharomyces cerevisiae* using CRISPR-Cas systems," Nucleic Acids Res, 2013, 1-8.
Doudna & Charpentier, "The new frontier of genome engineering with CRISPR-Cas9," Science, Nov. 2014, 346(6213):1258096, 10 pages.
Doyon et al, "Directed evolution and substrate specificity profile of homing endonuclease I-SceI," J. Am. Chem. Soc., 2006, 128:2477-2484.
Duan,et al., "Genome-wide identification of CRISPR/Cas9 off-targets in human genome," Cell Res, 2014, 24(8):1009-1012.

EP Extended European Search Report in Application No. 16845183.9, dated Jan. 18, 2019, 11 pages.
EP Extended European Search Report in Application No. 16852752.1, dated Feb. 20, 2019, 11 pages.
EP Extended European Search Report in European Application No. 15812186.3, dated Oct. 19, 2017, 7 pages.
EP Office Action in European Application No. 15812186.3, dated Jun. 15, 2018, 4 pages.
EP Office Action in European Appln. No. 15812186.3, dated Aug. 28, 2019, 4 pages.
EP Office Action in European Appln. No. 16852752.1, dated Jan. 29, 2020, 4 pages.
Esvelt et al, "Orthogonal Cas9 proteins for RNA-guided gene regulation and editing," Nat. Methods, Sep. 2013, 10:1116-1121.
Fonfara et al., "Phylogeny of Cas9 determines functional exchangeability of dual-RNA and Cas9 among orthologous type II CRISPR-Cas systems," 2014, Nucleic Acids Res 42(4): 2577-2590.
Frock et al., "Genome-wide detection of DNA double-stranded breaks induced by engineered nucleases," Nat Biotechnol, Feb. 2015, 33: 179-186.
Fu et al., "High-frequency off-target mutagenesis induced by CRISPR-Cas nucleases in human cells," Nat Biotechnol., 2013, 31:822-826 (Author Manuscript).
Fu et al., "Improving CRISPR-Cas nuclease specificity using truncated guide RNAs," Nat Biotechnol, Mar. 2014, 32(3): 279-284.
Gabriel et al., "An unbiased genome-wide analysis of zinc-finger nuclease specificity," Nat Biotechnol, Sep. 2011, 29(9): 816-823.
Gagnon et al, "Efficient mutagenesis by Cas9 protein-mediated oligonucleotide insertion and large-scale assessment of single-guide RNAs," PLoS One, 2014, 9, e98186.
Gaj et al., "ZFN, TALEN and CRISPR/Cas-based methods for genome engineering," Trends Biotechnol,, Jul. 2013, 31(7):397-405.
Gasiunas et al., "Cas9-crRNA ribonucleoprotein complex mediates specific DNA cleavage for adaptive immunity in bacteria," Proceedings of the National Academy of Sciences, Sep. 2012, E2579-E2586.
Gaudelli et al, "Programmable base editing of A•T to G•C in genomic DNA without DNA cleavage," Nature, Nov. 2017, 23;551(7681):464-471.
Ghezraoui et al., "Chromosomal translocations in human cells are generated by canonical nonhomologous end-joining," Mol Cell, Sep. 18, 2014, 55: 829-842.
Gnirke et al., "Solution hybrid selection with ultra-long oligonucleotides for massively parallel targeted sequencing," Nature Biotechnology, 2009, 27: 182-189.
Gori et al., "Delivery and Specificity of CRISPR-Cas9 Genome Editing Technologies for Human Gene Therapy," Hum Gene Ther, 2015, 26: 443-451.
Gostissa et al., "IgH class switching exploits a general property of two DNA breaks to be joined in cis over long chromosomal distances," Proc Natl Acad Sci, Feb. 18, 2014, 111(7): 2644-2649.
Guilinger et al., "Broad specificity profiling of TALENs results in engineered nucleases with improved DNA-cleavage specificity," Nat. Meth., Apr. 2014, 11(4):429-435.
Guilinger et al., "Fusion of catalytically inactive Cas9 to FokI nuclease improves the specificity of genome modification," Nat Biotechnol, Jun. 2014, 32(6): 577-582.
Hale et al, "Essential Features and Rational Design of CRISPR RNAs That Function With the Cas RAMP Module Complex to Cleave RNAs," Molecular Cell, Feb. 2012, 45(3):292-302.
Heigwer et al., "E-CRISP: fast CRISPR target site identification," Nat Methods, Feb. 2014, 11: 122-123.
Holtz et al., "APOBEC3G cytosine deamination hotspots are defined by both sequence context and single-stranded DNA secondary structure," Nucleic Acids Research, Jul. 2013, 41(12):6139-.
Horvath et al., "Diversity, activity, and evolution of CRISPR loci in *Streptococcus thermophiles*," J Bacteriol, 2008, 190, 1401-1412.
Hou et al, "Efficient genome engineering in human pluripotent stem cells using Cas9 from Neisseria meningitidis," Proc. Natl. Acad Sci USA, Sep. 2013, 110(39):15644-15649.
Hsu et al., "Development and Applications of CRISPR-Cas9 for Genome Engineering," Cell, 2014, 157(6):1262-1278.

(56) References Cited

OTHER PUBLICATIONS

Hsu et al., "DNA targeting specificity of RNA-guided Cas9 nucleases," Nat Biotechnol., 2013, 31:827-832.
Hwang et al., "Efficient In Vivo Genome Editing Using RNA-Guided Nucleases," Nat Biotechnol., 2013, 31:227-229 (Author Manuscript).
IL Office Action In Israeli Appln. No. 249555, dated Dec. 16, 2019, 6 pages (with English translation).
IL Office Action In Israeli Appln. No. 257955, dated May 1, 2020, 6 pages (with English translation).
Ishino et al, "Identification of a mismatch-specific endonuclease in hyperthermophilic Archaea," Nucleic Acids Res., Apr. 2016, 44(7): 2977-2986.
Jiang et al., "Characterization of *Escherichia coli* Endonuclease VIII," J. Biol. Chem, 1997, 272:32230-32239.
Jiang et al., "CRISPR-assisted editing of bacterial genomes," Nat Biotechnol, Mar. 2013, 31(3):233-239.
Jinek et al., "A programmable dual-RNA-guided DNA endonuclease in adaptive bacterial immunity," Science, 2012, 337:816-821.
Jinek et al., "RNA-programmed genome editing in human cells," Elife, 2013, 2:e00471, 9 pages.
JP Office Action in Japanese Appln. No. 2016-575174, dated Jul. 9, 2019, 12 pages (with English translation).
JP Office Action in Japanese Appln. No. 2016-575174, dated May 12, 2020, 6 pages (with English translation).
Keegan et al, "ADAR RNA editing below the backbone," RNA, Sep. 2017, 23(9):1317-1328.
Kim et al, "Increasing the genome-targeting scope and precision of base editing with engineered Cas9-cytidine deaminase fusions," Nat Biotechnol., Apr. 2017, 35(4):371-376.
Kim et al., "Genome-wide target specificities of CRISPR RNA-guided programmable deaminases," Nat. Biotech., May 2017, 35(5):475-480.
Kim et al., "Genome-wide target specificity of CRISPR RNA-guided adenine base editors," Nature Biotechnology, Apr. 2019, 37(4):430-435.
Kim et al., "Digenome-seq: genome-wide profiling of CRISPR-Cas9 off-target effects in human cells," Nat Meth, Mar. 2015, 12: 237-243.
Kim et al., "Genome-wide target specificities of CRISPR-Cas9 nucleases revealed by multiplex Digenome-seq," Genome Res, 2016, 26: 406-415.
Kleinstiver et al., "A unified genetic, computational and experimental framework identifies functionally relevant residues of the homing endonuclease I-Bmol," Nucleic Acids Res., 2010, 38(7):2411-2427.
Kleinstiver et al, "Broadening the targeting range of *Staphylococcus aureus* CRISPR-Cas9 by modifying PAM recognition," Nature, Dec. 2015, 33(12):1293-1298.
Kleinstiver et al, "Engineered CRISPR-Cas9 nucleases with altered PAM specificities," Nature, Jun. 2015, 523(7561):481-485.
Kleinstiver et al., "High-fidelity CRISPR-Cas9 nucleases with no detectable genome-wide off-target effects," Nature, Jan. 2016, 529: 490-495.
Komor et al, "Improved base excision repair inhibition and bacteriophage Mu Gam protein yields C:G-to-T:A base editors with higher efficiency and product purity," Sci. Adv., Aug. 2017, 3:eaao4774, 9 pages.
Komor et al, "Programmable editing of a target base in genomic DNA without double-stranded DNA cleavage," Nature, May 2016,533(7603):420-424.
Kuraoka "Diversity of Endonuclease V: From DNA Repair to RNA Editing" Biomolecules, Dec. 2015, 5(4):2194-2206.
Kuscu et al., "Genome-wide analysis reveals characteristics of off-target sites bound by the Cas9 endonuclease," Nat Biotechnol, Jul. 2014, 32 (7): 677-683.
Lazzarotto et al., "Defining CRISP-Cas9 genome-wide nuclease activities with Circle-seq," Nature Protocols, Oct. 2018, 13: 2615-2642.

Liang et al., "Genome-wide profiling of adenine base editor specificity by EndoV-seq," Nature Communications, Jan. 2019, 10(1):67, 9 pages.
Lin et al., "CRISPR/Cas9 systems have off-target activity with insertions or deletions between target DNA and guide RNA sequences," Nucleic Acids Res, 2014, 42(11): 7473-7485.
Lindahl et al., "DNA N-glycosidases: properties of uracil-DNA glycosidase from *Escherichia coli*," J. Biol. Chem., May 1977, 252:3286-3294.
Lindahl, "DNA repair enzymes," Annu. Rev. Biochem, 1982, 51:61-64.
Makarova et al., "Evolution and classification of the CRISPR-Cas systems," Nature Reviews Microbiology, Jun. 2011, 9(6):467-477.
Mali et al., "CAS9 transcriptional activators for target specificity screening and paired nickases for cooperative genome engineering," Nat Biotechnol, Sep. 2013, 31(9): 833-838.
Mali et al., "RNA-guided human genome engineering via Cas9," Science, Feb. 2013, 339:823-826 (Author Manuscript).
Marx et al., "Gene editing: how to stay on-target with CRISPR," Nat Methods, 2014, 11:1021-1026.
Melamede et al., "Isolation and characterization of endonuclease VIII from *Escherichia coli*," Biochemistry, Feb. 1994, 33:1255-1264.
Miller et al. "A TALE nuclease architecture for efficient genome editing," Nat. Biotech., Feb. 2011, 29(2):443-150.
Mojica et al., "Short motif sequences determine the targets of the prokaryotic CRISPR defence system," Microbiology, Jan. 2009, 155:733-740.
Mullis and Faloona, "Specific synthesis of DNA in vitro via a polymerase-catalyzed chain reaction," Methods in Enzymology, 1987, 155: 335-350.
Nhm.ac.uk [online], "Blunting of DNA" Nov. 11, 2012, retrieved on Apr. 14, 2020, retrieved from URL <https://www.nhm.ac.uk/content/dam/nhmwww/our-science/dpts-facilities-staff/Coreresearchlabs/blunting-of-dna_aug12.pdf>, 1 page.
Nishida et al, "Targeted nucleotide editing using hybrid prokaryotic and vertebrate adaptive immune systems," Science, Sep. 2016, 53(6305), 14 pages.
Nishimasu al, "Crystal Structure of Cas9 in Complex with Guide RNA and Target DNA," Feb. 2014, Cell 156(5):935-949.
Ochman et al., "Genetic Applications of an Inverse Polymerase Chain Reaction," Genetics, Nov. 1998, 120:621-623.
Oliphant et al., "Defining the sequence specificity of DNA-binding proteins by selecting binding sites from random-sequence oligonucleotides: analysis of yeast GCN4 protein," Mol. Cell. Biol., Jul. 1989, 9(7):2944-2949.
Orlando et al., "Zinc-finger nuclease-driven targeted integration into mammalian genomes using donors with limited chromosomal homology," Nucleic Acids Res, 2010, 38(15): e152.
Osborn et al., "TALEN-based gene correction for epidermolysis bullosa," 2013, Mol Ther, 21: 1151-1159.
Pattanayak et al., "High-throughput profiling of off-target DNA cleavage reveals RNA-programmed Cas9 nuclease specificity," Nat Biotechnol., 2013, 31:839-843 (Author Manuscript).
Pattanayak et al., "Revealing off-target cleavage specificities of zinc-finger nucleases by in vitro selection," Nat. Meth., 8(9):765-770.
PCT International Preliminary Report on Patentability in International Application No. PCT/US2016/051097, dated Mar. 13, 2018, 10 pages.
PCT International Preliminary Report on Patentability in International Application No. PCT/US2016/054912, dated Apr. 12, 2018, 10 pages.
PCT International Preliminary Report on Patentability in International Application No. PCT/US2018/047577, dated Feb. 25, 2020, 8 pages.
PCT International Preliminary Report on Patentability in International Appln. No. PCT/US2018/055406, dated Apr. 14, 2020, 8 pages.
PCT International Search Report and Written Opinion in International Application No. PCT/US15/37269, dated Oct. 15, 2015, 26 pages.

(56) References Cited

OTHER PUBLICATIONS

PCT International Search Report and Written Opinion in International Application No. PCT/US16/51097, dated Jan. 24, 2017, 12 pages.
PCT International Search Report and Written Opinion in International Application No. PCT/US16/54912, dated Jan. 24, 2017, 12 pages.
PCT International Search Report and Written Opinion in International Application No. PCT/US19/27788, dated Aug. 5, 2019, 19 pages.
PCT International Search Report and Written Opinion in International Appln. No. PCT/US18/55406, dated Jan. 17, 2019, 10 pages.
Perez et al., "Establishment of HIV-1 resistance in CD4+ T cells by genome editing using zinc-finger nucleases," Nat. Biotech., Jul. 2008, 26(7):808-816.
Pinello et al., "Analyzing CRISPR genome-editing experiments with CRISPResso," Nat. Biotechnol., Jul. 2016, 34(7): 695-697.
Ran et al., "Double nicking by RNA-guided CRISPR Cas9 for enhanced genome editing specificity," Cell, Sep. 2013, 154: 1380-1389.
Ran et al., "Genome engineering using the CRISPR-Cas9 system," Nat Protoc, Nov. 2013, 8(11): 2281-2308.
Ran et al., "In vivo genome editing using *Staphylococcus aureus* Cas9," Nature, Apr. 2015, 520, 186-191.
Rebhandl et al., "AID/APOBEC Deaminases and Cancer." Oncoscience, Apr. 2015, 2(4):320-333.
Reyon et al, "FLASH assembly of TALENs for high-throughput genome editing," Nat. Biotechnol., May 2012, 30(5):460-465.
Sander and Joung et al., "CRISPR-Cas systems for editing, regulating and targeting genomes," Nat Biotechnol., Apr. 2014, 32(4):347-55.
Sander et al., "In silico abstraction of zinc finger nuclease cleavage profiles reveals an expanded landscape of off-target sites," Nucleic Acids Res, Oct. 2013, 41(19): e181.
Sapranauskas et al, "The *Streptococcus thermophilus* CRISPR/Cas system provides immunity in *Escherichia coli*," Nucleic Acids Res., Aug. 2011, 39(21):9275-9282.
Sawa et al., "The ADAR protein family," Genome Biol., Dec. 2012, 13(12):252, 10 pages.
Schaub and Keller, "RNA editing by adenosine deaminases generates RNA and protein diversity," Biochimie, Aug. 2002, 84(8):791-803.
Schmidt et al., "High-resolution insertion-site analysis by linear amplification-mediated PCR (LAM-PCR)," Nat Methods, Dec. 2007, 4(12): 1051-1057.
Shah et al., "Protospacer recognition motifs," RNA Biol., Feb. 2013, 10(5):891-899.
Shen et al., "Generation of gene-modified mice via Cas9/RNA-mediated gene targeting," Cell Res, 2013,23:720-723.
Shinohara et al., "APOBEC3B can impair genomic stability by inducing base substitutions in genomic DNA in human cells." Scientific Reports, Nov. 2012, 2(806), 10 pages.
Slaymaker et al, "Rationally engineered Cas9 nucleases with improved specificity," Science, Jan. 2016, 1;351(6268):84-88.
Sloan et al., "Detecting rare mutations and DNA damage with sequencing-based methods," Trends in Biotechnology, Jul. 2018, 36(7):729-740.
Smith et al., "Whole-genome sequencing analysis reveals high specificity of CRISPR/Cas9 and TALEN-based genome editing in human iPSCs," Cell Stem Cell, Jul. 3, 2014, 15(1):12-13.
Sternberg et al, "DNA interrogation by the CRISPR RNA-guided endonuclease Cas9," Nature, Jan. 2014, 507(7490):62-67.
Suspène et al., "Erroneous Identification of APOBEC3-edited Chromosomal DNA in Cancer Genomics," British Journal of Cancer, May 2014, 110(10):2615-2622.
Suspene et al., "Extensive editing of both hepatitis B virus DNA strands by APOBEC3 cytidine deaminases in vitro and in vivo." Proceedings of the National Academy of Sciences of the United States of America, Jun. 2005, 102(23):8321-8326.
Suspene et al., "Recovery of APOBEC3-edited human immunodeficiency vims G→A hypermutants by differential DNA denaturation PCR." Journal of General Virology, Jan. 2005, 86(1):125-129.
Thakore et al., "Highly specific epigenome editing by CRISPR-Cas9 repressors for silencing of distal regulatory elements," Nat. Meth., Dec. 2015, 12(12):1143-1149.
Thermofisher.com {online}. "PCR Methods-Top Ten Strategies," 2017, [retrieved on Feb. 1, 2017], Retrieved from the Internet: URL<https://www.thermofisher.com/us/en/home/life-science/cloning/cloning-learningcenter/invitrogen-school-of-molecular-biology/per-education/per-reagents-enzymes/per-methods.html>, 10 pages.
Tsai and Joung, "Defining and improving the genome-wide specificities of CRISPR-Cas9 nucleases," Nature, Apr. 2016, 17: 300-312.
Tsai et al., "Circle-seq: a highly sensitive in vitro screen for genome-wide CRISPR-Cas9 nuclease off-targets," Nature Methods, May 2017, 14: 607-614.
Tsai et al., "Dimeric CRISPR RNA-guided FokI nucleases for highly specific genome editing," Nat Biotechnol, Jun. 2014, 32(6): 569-576.
Tsai et al., "Guide-seq Enables Genome-Wide Profiling of Off-Target Cleavage by CRISPR-Cas Nucleases," Nature Biotechnology, Dec. 2014, 187-197.
Tsai et al., "What's changed with genome editing?," Jul. 2014, Cell Stem Cell, 15(1):3-4.
Vakulskas et al, "A high-fidelity Cas9 mutant delivered as a ribonucleoprotein complex enables efficient gene editing in human haematopoietic stem and progenitor cells," Nature Medicine, Aug. 2018, 24(8):4216-1224.
Veres et al., "Low incidence of off-target mutations in individual CRISPR-Cas9 and TALEN targeted human stem cell clones detected by whole-genome sequencing," Cell Stem Cell, Jul. 3, 2014, 15: 27-30.
Vierstra et al, "Functional footprinting of regulatory DNA," Nat. Methods, Oct. 2015, 12(10):927-30.
Wiedenheft et al, "RNA-guided genetic silencing systems in bacteria and archaea" Nature, Feb. 2012, 482:331-338.
Wolf et al, "tadA, an essential tRNA-specific adenosine deaminase from *Escherichia coli*," EMBO J., Jul. 2002, 21(14):3841-3851.
Wu et al. "Evolution of Inosine-Specific Endonuclease V from Bacterial DNase to Eukaryotic RNase" Molecular Cell, Oct. 2019, 76(1):44-56.
Wu et al., "Genome-wide binding of the CRISPR endonuclease Cas9 in mammalian cells," Nat Biotechnol. Jul. 2014; 32(7):670-6.
Yang et al. "Engineering and optimising deaminase fusions for genome editing" Nature Communications, Nov. 2016, 7(1):1-12.
Yang et al., "Targeted and genome-wide sequencing reveal single nucleotide variations impacting specificity of Cas9 in human stem cells," Nature Communications, Nov. 2014, 5: 5507.
Zentner & Henikoff, "Epigenome editing made easy," Nat. Biotech., Jun. 2015, 33(6):606-607.
Zhang et al, "Processing-Independent CRISPR RNAs Limit Natural Transformation in Neisseria meningitidis," Mol. Cell 50, May 2013, 488-503.
Zheng et al., "Anchored multiplex PCR for targeted next-generation sequencing," Nat Med, Nov. 10, 2014, 20(12): 1479-1484.
Du et al., "Quantitative assessment of HR and NHEJ activities via CRISPR/Cas9-induced oligodeoxynucleotide-mediated DSB repair," DNA Repair, Sep. 2018, 70:67-71.
Tsai et al., "Supplementary Information: Guide-seq Enables Genome-Wide Profiling of Off-Target Cleavage by CRISPR-Cas Nucleases," Nature Biotechnology, Jun. 2015, 52 pages.

\* cited by examiner

METHODS FOR DETECTING SITE-SPECIFIC AND SPURIOUS GENOMIC DEAMINATION INDUCED BY BASE EDITING TECHNOLOGIES

CLAIM OF PRIORITY

This application is a § 371 National Stage Application of PCT/US2018/055406, filed Oct. 11, 2018, which claims the benefit of U.S. Provisional Application Ser. No. 62/571,222, filed Oct. 11, 2017. The entire contents of the foregoing are incorporated herein by reference.

FEDERALLY SPONSORED RESEARCH OR DEVELOPMENT

This invention was made with Government support under Grant Nos. GM118158 and HG009490 awarded by the National Institutes of Health. The Government has certain rights in the invention.

TECHNICAL FIELD

Described herein are methodologies to detect off-target mutations induced by the deaminase activity of Base Editing technology.

BACKGROUND

Base editing (BE) technologies use an engineered DNA binding domain such as zinc finger arrays or RNA-guided, enzymatically inactivated or deficient DNA binding protein such as nickase Cas9 (nCas9) to recruit a cytidine deaminase domain to a specific genomic location to effect site-specific cytosine→thymine transition substitutions[1,2].

SUMMARY

The present invention is based on the development of methodologies to detect off-target mutations induced by the deaminase activity of Base Editing technology. Two methods are described. The first involves an in vitro Base-Editor targeting and deamination reaction of representative DNA populations followed by an enzymatic digestion specific to G:U mismatches and sequencing of the digested species, which will yield data on the types of targets that the full Base Editor enzyme can target and deaminate. The second is a targeted PCR-based enrichment protocol that will allow for the selective amplification of rare, yet important, genomic deamination-induced mutations that could arise from Base Editor's deaminase domain acting independently of any site-specific targeting by its engineered DNA binding domain. We also claim that this last technology may be further applicable to sense rare deletion events mediated by traditional double-stranded-break-inducing genome-editing nuclease technologies.

Thus, provided herein are methods for detecting deaminated sites in substrate DNA. The methods include providing a sample comprising substrate DNA, e.g., genomic DNA (gDNA) or synthesized DNA; deaminating the substrate DNA using a base editing fusion protein comprising a deaminase domain and a DNA binding domain, e.g., a zinc-finger domain; a transcription-activator-like effector domain; or a catalytically-inactive Cas9 or Cpf1, with a selected guide RNA, e.g., an sgRNA of interest; contacting the deaminated substrate with Endonuclease MS from *Thermococcus kodakarensis* (TkoEndoMS) to induce double strand breaks (DSBs) at deamination sites in the substrate DNA to produce DNA fragments with single-stranded, 5 base pair overhanging ends centered at the deamination site; treating the DNA fragments with uracil DNA glycosylase and endonuclease VIII to remove the deoxyuracil base from the ends of the DNA fragments; end-repairing and/or A-tailing the ends of the DNA fragments; and ligating an adapter oligonucleotide (preferably comprising sequences for use in high throughput sequencing) to the end; and sequencing the DNA fragments.

Also provided herein are methods for detecting deaminated sites in substrate DNA. The methods include providing a sample comprising substrate DNA; deaminating the substrate DNA using a base editing fusion protein comprising a deaminase domain, e.g., genomic DNA (gDNA) or synthesized DNA, and a nicking Cas9 protein (nCas9); contacting the deaminated substrate DNA with uracil DNA glycosylase and endonuclease VIII, to induce DSBs; end-repairing and/or A-tailing the ends of the DNA fragments; ligating adapter oligonucleotide (comprising sequences for use in high throughput sequencing) to the end; and sequencing the DNA fragments.

In some embodiments of the methods described herein, the adapter oligonucleotide comprises a single deoxyuridine, e.g., as described in US PG Pub. 2017/0088833. In some embodiments of the methods described herein, the adapter oligonucleotides comprise PCR primer binding sequences, and the methods comprises using PCR to enrich for sites that produced a DSB.

In some embodiments of the methods described herein, sequencing the DNA fragments comprises determining a sequence of at least about (i.e., ±10%) 10, 15, 20, 30, 50, 100, 150, 200, 250, 500, or more nucleotides at the ends of the DNA fragments.

In addition, provided herein are methods for detecting and quantifying base editor-induced cytosine to thymine mutation events in living cells. The methods include providing a sample comprising substrate genomic DNA from cells exposed to a base editor protein comprising a deaminase domain fused to DNA binding domain, e.g., a zinc-finger domain; a transcription-activator-like effector domain; or a Cas9 or Cpf1 nickase or catalytically-inactive Cas9 or Cpf1, with a selected guide RNA, e.g., an sgRNA of interest; using 3D PCR to selectively amplify alleles that have undergone deamination events, to create a population of amplicons that is enriched for deaminated alleles; and sequencing the enriched population of amplicons, preferably using next generation sequencing or TOPO cloning, to determine the identity of the amplified molecules. In some embodiments of the methods described herein, using 3D PCR to selectively amplify alleles that have undergone deamination events comprises shearing the substrate genomic DNA; ligating barcoded common adapters to the free ends of the sheared genomic DNA; and amplifying sites of interest with 3D PCR using one site-specific primer and one adapter-specific primer.

In some embodiments, the substrate genomic DNA is sheared randomly or semi-randomly using sonication or enzymatic treatment.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1. Unbiased, genome-wide in vitro method for discovering all off-target deamination events induced by BEs. Briefly, sheared genomic DNA (gDNA) is ligated to hairpin adaptors at both ends. After treatment with Lambda exo/ExoI to remove gDNA fragments, the hairpin adaptors are opened via treatment with USER enzyme to excise an internal uracil base and the resulting single stranded ends are used to circularize the gDNA-adaptor fragments via ligation. Treatment with Plasmid-Safe DNase removes all uncircularized DNA, leaving a homogenous population of circular gDNA fragments with a mean length of 300 base pairs. This population is then treated with purified BE protein in complex with an sgRNA of interest for two hours at 37C to induce deamination at on- and off-target sites. Treatment of the deaminated DNA with TkoEndoMS creates DNA double strand breaks at all deamination sites. A second treatment with USER enzyme removes all BE-induced uracils, and DNA end repair and A-tailing produce suitable substrates for ligation to high throughput sequencing adaptors at each deamination site. PCR product enriched for on- and off-target site deamination events is subjected to high throughput sequencing and bioinformatic characterization to discover all in vitro deamination sites. Note that this strategy can also be adapted to use a nicking base editor protein. In this case, a DSB is generated by treatment with USER enzyme following deamination of the substrate DNA.

DETAILED DESCRIPTION

Base editing (BE) technologies use an engineered DNA binding domain (such as RNA-guided, catalytically inactive Cas9 (dead Cas9 or dCas9), a nickase version of Cas9 (nCas9), or zinc finger (ZF) arrays) to recruit a cytidine deaminase domain to a specific genomic location to effect site-specific cytosine→thymine transition substitutions[1,2]; see also U.S. Ser. 62/541,544, which is incorporated herein by reference.

Since the deaminase domains used in BEs preferentially act on single-stranded DNA (ssDNA) substrates, it is thought that BEs that use nCas9 to direct their genomic targeting will be the most efficient configuration because nCas9-targeting involves the hybridization of a short guide RNA (sgRNA) to its genomic target and the concurrent displacement of the non-target strand into ssDNA in an R-loop. Like any other genome-editing technology, fully understanding a BE's ability to induce off-target mutations is an important step toward developing it for clinical applications; however, the subtle nature of the C→T mutation and the sheer number of cytosines that exist in the genome make BE's off-target mutations more difficult to detect than the off-target mutations induced by other kinds of genome-editing technologies.

With first-generation BE technology, we have identified three major potential sources of off-target mutagenesis. First, BE nCas9-stimulated R-loop formation can expose a total of 8 on-target nucleotides for deamination (5 of which having more-or-less equivalent propensities for mutagenesis) even though it may sometimes be necessary to restrict BE's mutagenic potential to only one target cytosine at a time. Second, Cas9 has a well-documented ability to bind at off-target sites with varying degrees of homology to its sgRNA[3-4], which could lead to off-target R-loop formation and subjection of non-target cytosines to deamination. Third, BE's deaminase component could act upon naturally occurring genomic ssDNA or RNA substrates independent of Cas9-mediated targeting, resulting in spurious deamination.

Recently, a group described an in vitro strategy to evaluate off-target activities of BEs at sites which were both deaminated by the DA domain and nicked by nCas9[5]. Because it fails to detect sites which have been deaminated but not nicked, this strategy incompletely describes off-target deamination sites for these technologies, and has no ability to detect mutations that derive from spurious deamination. In addition, this method's general insensitivity and requirement for whole genome sequencing at 30-40× coverage for each sgRNA assessed makes it too cumbersome and expensive to be reasonably performed by most research laboratories and/or companies who may need to assess many BE:sgRNA complexes simultaneously. Here, we describe two new highly sensitive BE off-target deamination detection methodologies that will collectively enable the assessment of this critical parameter necessary for maturing BE toward therapeutic relevance, where modification of millions to billions of cells might be necessary.

Figure 1:
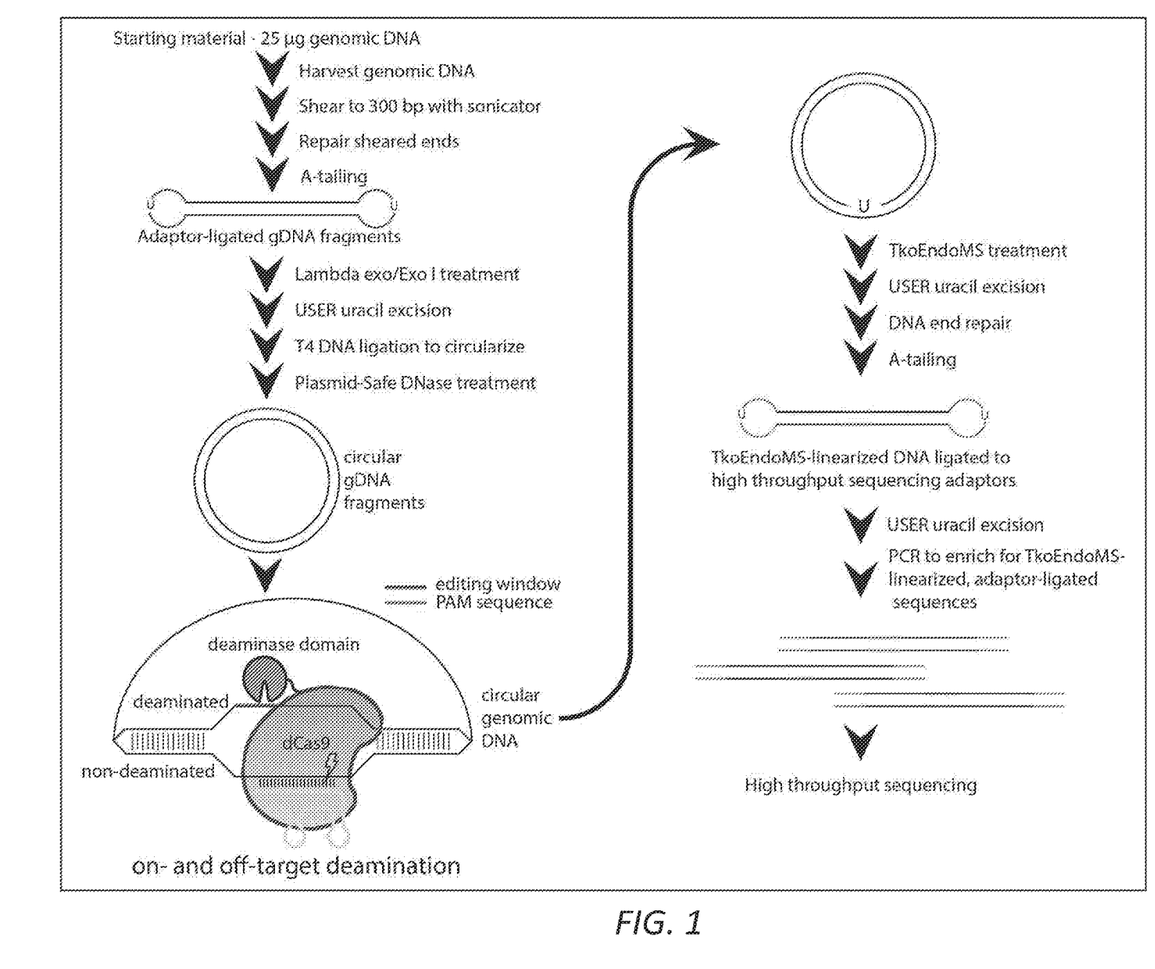

Method 1: Detecting Deamination Events Induced by BE Technologies at Off-Target nCas9 or dCas9 Sites To describe all possible off-target deamination events induced by BE technologies in a sensitive and practical manner, an in vitro method modified from a previous in vitro assay for detecting off-targets of RNA-guided nucleases (CIRCLE-Seq[6]) can be used. This assay uses sheared, circularized genomic DNA (gDNA) or synthesized linear DNA as a reporter substrate for deamination events (FIG. 1). See also US PG Pub. 2017/0088833, which is incorporated herein in its entirety. In the modified assay, the substrate gDNA or synthesized DNA is deaminated by purified BE protein (consisting of a fusion protein between a deaminase domain and a DNA binding domain, e.g., a zinc finger, TALE, or catalytically-inactive Cas9 or Cpf1, e.g., as described in WO 2017/059313) in complex with an sgRNA of interest. TkoEndoMS, a protein derived from *Thermococcus kodakarensis* that has previously been shown to recognize G:T mismatches[7] and that we have shown efficiently recognizes the G:U mismatch resulting from a BE deamination event (FIG. 2), is then used to induce double strand breaks (DSBs) at all deamination sites in the substrate DNA. The DSB induced by TkoEndoMS in the substrate gDNA produces two ends that, after repair and A-tailing, are suitable substrates for ligation to high throughput sequencing adaptors, allowing for the capture, enrichment and sequencing of these sites. Because this strategy relies solely on the presence of a G:U mismatch, it will capture all deamination sites induced by BEs in the substrate DNA, resulting in a more complete activity profile of these technologies for use in research and therapeutics.

Alternatively, the substrate gDNA or synthesized DNA is deaminated by purified BE protein composed of a deaminase domain and a nicking Cas9 protein. A DSB is then generated by treating the deaminated substrate DNA with USER enzyme (a mixture of uracil DNA glycosylase and endonuclease VIII), a reagent that specifically catalyzes the removal of uracil bases from DNA. This strategy produces two DNA ends that, following end repair, A-tailing, and ligation to high-throughput sequencing adapters, are compatible for PCR to enrich for sites that produced a DSB followed by deep sequencing.

Figure 3:
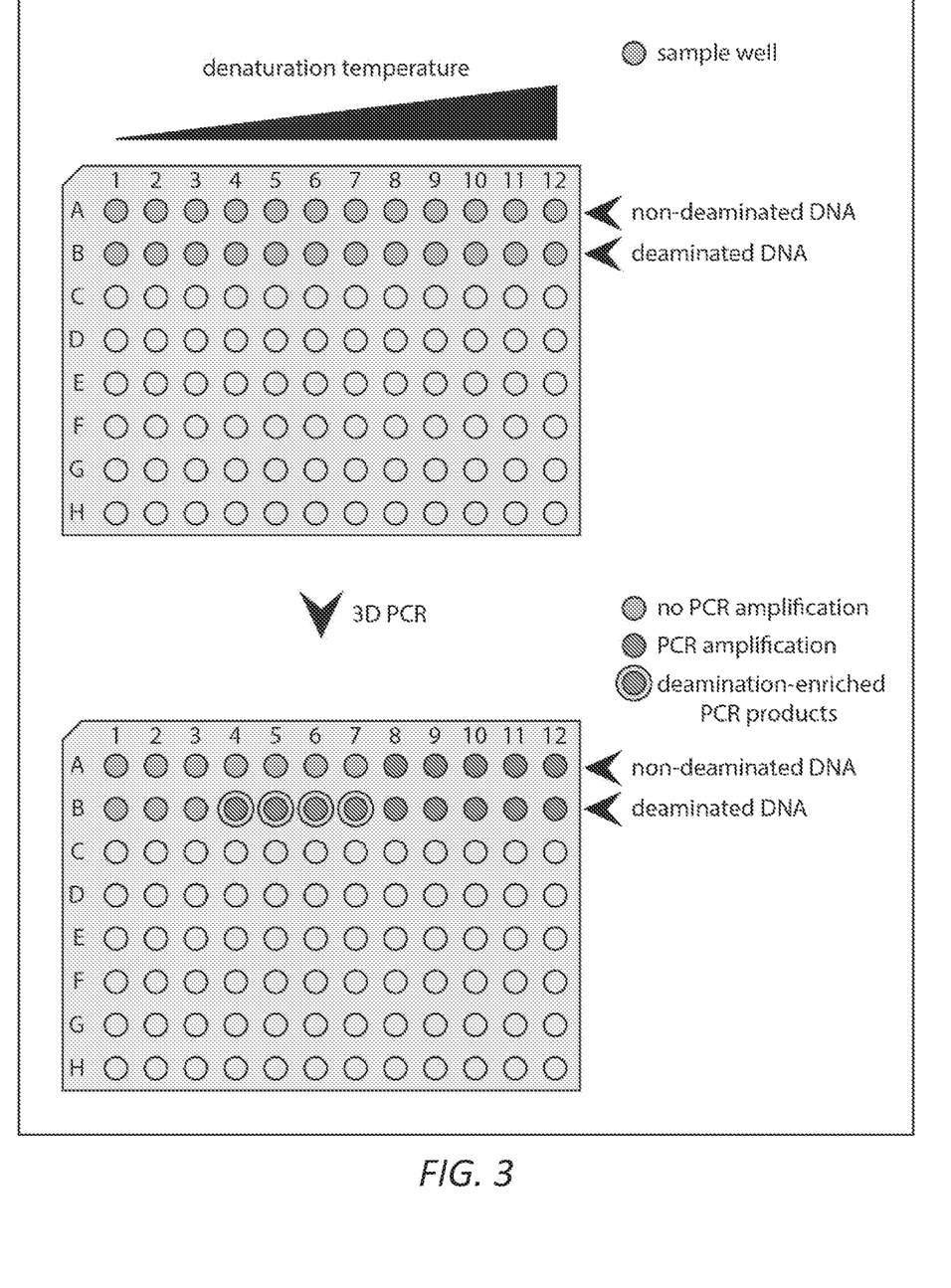
FIG. 3. 3D PCR uses a gradient of denaturation temperatures in otherwise standard PCR cycles applied across a 96-well plate. Each row contains 12 replicates of the same sample, and the left-most sample that successfully amplifies contains a library of PCR products derived from deaminated genomic DNA. The DNA in row A is unable to amplify at the same low temperatures because it does not contain deaminated genomic DNA.

Method 2: Detection of Spurious Deamination Events Induced by BE Technologies at Genomic Off-Target Sites Independent of nCas9 Targeting Using 3D PCR Because of the sheer number of cytosines in a genome, the relative odds that any given cytosine will be mutated by spurious deamination by BE technologies may remain extremely limited even if spurious deamination is a ubiquitous phenomenon with a high cumulative total of deamination events among all cells exposed to BE. Due to the error rate of Illumina sequencing methods, BE-induced mutation events that occur at a given genomic cytosine in fewer than 1 in ~1000 cells will be undetectable by standard whole genome sequencing or PCR amplicon-based deep sequencing strategies[3]. One technique that has been described previously to enrich for extremely rare deamination events takes advantage of the differential DNA denaturation temperatures between deaminated amplicons containing slightly higher A:T content than their non-deaminated counterparts[8-10]. In this method, referred to as differential DNA denaturation PCR (3D PCR), the denaturation component of a standard PCR cycle is varied in a gradient across a row of PCR tubes or 96-well plate in order to find the lower limit for denaturation of the target amplicon. In complex samples containing very low numbers of amplicons in which deamination events have increased the A:T content, this allows for selective denaturation and exponential amplification of very rare deaminated amplicons (FIG. 3). The products from the lowest denaturation temperature 3D PCRs can then be subjected to high-throughput sequencing to determine which nucleotides within the amplicon have undergone C→T transition mutations. The sequencing can be done via a high-throughput strategy like Illumina sequencing, or using TOPO cloning, e.g., by inserting individual molecules from the 3D PCR population into plasmids and propagating those plasmids in bacteria, then sequencing those plasmids/inserts to determine the identity of the 3D PCR population of molecules.

Figure 4:
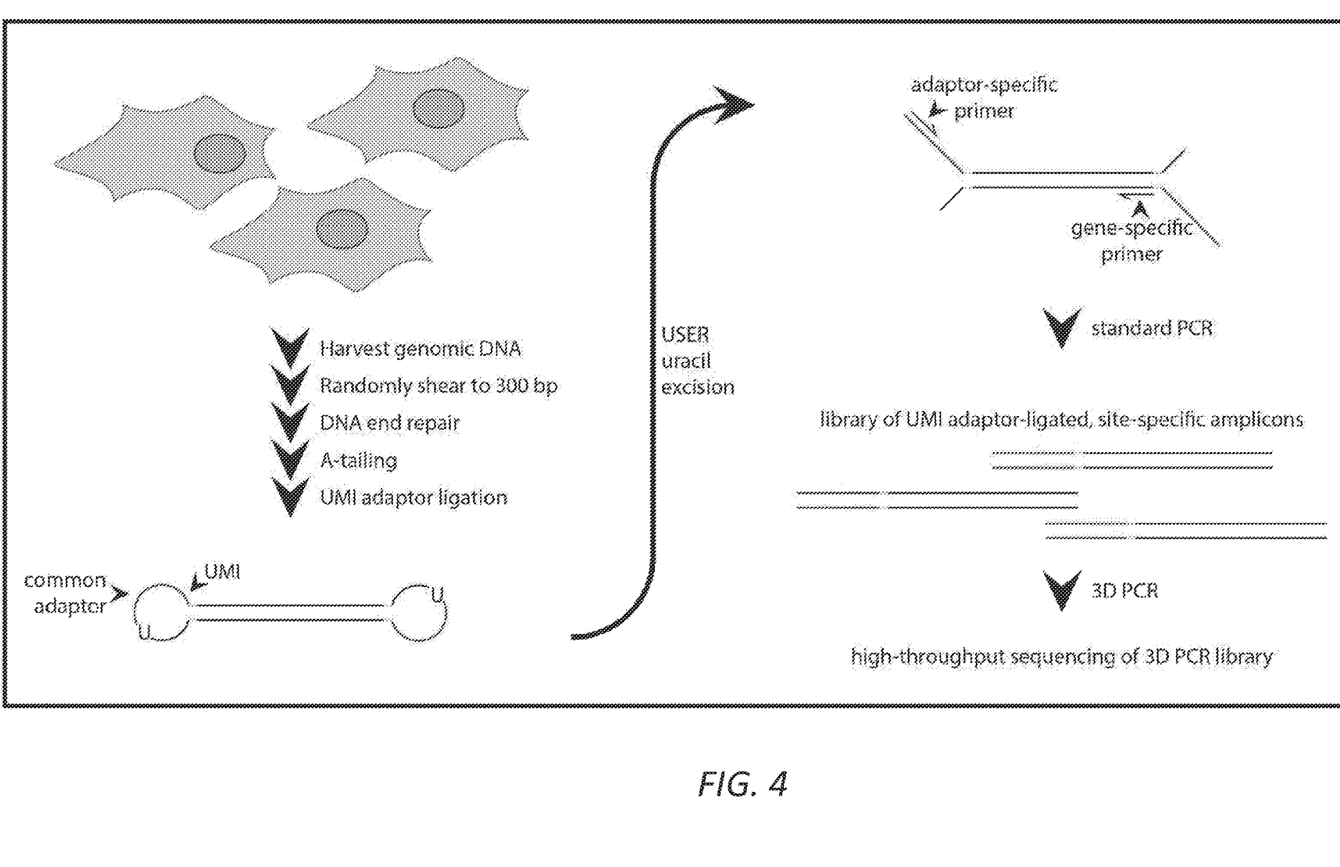
FIG. 4. Schematic of modified 3D PCR with unique molecular indices to enable de-duplication of the high-throughput sequencing library. De-duplication allows for the bioinformatic determination of the total number of alleles with deamination events from the harvested genomic DNA.

The 3D PCR method can selectively enrich for genomic sequences bearing C→T mutations and can be used to amplify and reliably detect rare deamination events in genomic DNA. However, PCR bias using current 3D PCR makes it difficult or impossible to determine the absolute rate of spurious deamination-mediated mutation events at a given locus. This is a critical parameter to quantify before any BE technologies can be deemed safe enough to use in therapeutic settings. Thus, the 3D PCR technique can be modified to selectively enrich for DNA amplicons that have undergone deamination events to assess the frequency of spurious deamination on a site-by-site basis. By creating 3D PCR substrates from the genomic DNA of deaminase-treated cells that has been randomly sheared and then ligated to hairpin adaptors containing a unique molecular index, we can quantify the number of alleles in a population that have undergone rare spurious deamination events by de-duplicating the reads obtained from high throughput sequencing of the 3D PCR library (FIG. 4).

While sampling issues may complicate this effort, careful determination as to the number of genomes' worth of DNA that are input into each UMI adaptor ligation and subsequent 3D PCR should yield a reasonably accurate number from which to calculate the spurious deamination rate. Others have previously calculated the enrichment factor of 3D PCR to be ~$10^4$, see ref[11], which would theoretically reduce the detection limit of spurious deamination events from ~$10^{-3}$ (from Illumina sequencing's error rate) to ~$10^{-7}$. Since a reasonable upper limit for the number of genomes input into a PCR is $10^5$ (approximately 400 ng of human gDNA), this method allows oversampling of any given deamination event by 100-fold. Simply dividing the number of distinct UMIs associated with reads containing C→T mutations in the 3D PCR Illumina sequencing data divided by the total number of UMIs observed in sequencing data of a parallel non-enriched PCR reaction on a similarly representative sample of DNA should yield the rate of BE-induced deamination events that occurred within that amplicon. We note that having enough unique UMIs such that there are ~10× as many UMIs as possible genomic ligation partners will ensure a very low number of duplicate UMI usage (~0.4% odds of any UMI being duplicated, by Poisson distribution) and therefore enable consistently precise calculations of the deamination error rates. Since a reasonable upper limit of input genomes is $10^5$, a 10 base pair random UMI containing $4 \times 10^{10}$ unique members will almost always satisfy this condition.

Because the lower limit of template DNA denaturation must be determined empirically for each 3D PCR amplicon, the technique allows only for detection of spurious deamination at sites specified by the gene-specific primer in the 3D PCR reaction and may be difficult to scale to whole genome sequencing. However, we believe that by targeting genomic 'hotspots' known to be highly susceptible to deamination and/or sites that are particularly sensitive to spurious deamination[12-13] (i.e., sites at which deamination results in oncogene expression), we can calculate an upper bound on genome-wide spurious deamination events and of spurious deamination events at sites which are likely to produce a disease phenotype.

This technique could be adapted to increase the sensitivity of on- and off-target detection for traditional nuclease-based genome-editing technologies. The in vitro discovery method of Cas9-mediated off-target mutagenesis called CIRCLE-Seq[6] is thought to be able to discover the nearly complete suite of genomic off-target sites for to a given Cas9:sgRNA complex. However, validating off-target mutagenesis at sites where the mutation frequency is below 1 in ~10,000 genomes has proven extremely challenging due to the intrinsic error rate of high throughput sequencing technology and the inability to enrich for these low frequency events in large populations. Therefore, some of the sites that CIRCLE-Seq identifies as off-targets are speculative and cannot be verified by targeted deep-sequencing. The combined UMI-ligation/3D PCR approach as described earlier in this section significantly improves on this 1 in ~1000 detection limit. Since Cas9 frequently induces short deletions at on- and off-target sites, amplicons containing Cas9-mediated mutations can be enriched compared to unmodified DNA. Previous groups have reported that 1 C→T mutation per 250 base pairs of DNA causes a large enough differential PCR template denaturation temperature over unmodified DNA to become enriched in 3D PCR, so it stands to reason a 1 base pair deletion in 250 base pairs can also be enriched.[14] In this scenario, the gene-specific priming will occur at a site predicted to be a Cas9 off-target site instead of one where we suspect spurious deamination has occurred. If the same enrichment factor of $10^4$ remains true of 3D PCR when used to selectively amplify sequences containing small deletions, the new off-target mutagenesis detection limit should be on the order of $10^{-7}$.

EXAMPLES

The invention is further described in the following examples, which do not limit the scope of the invention described in the claims.

Figure 2:
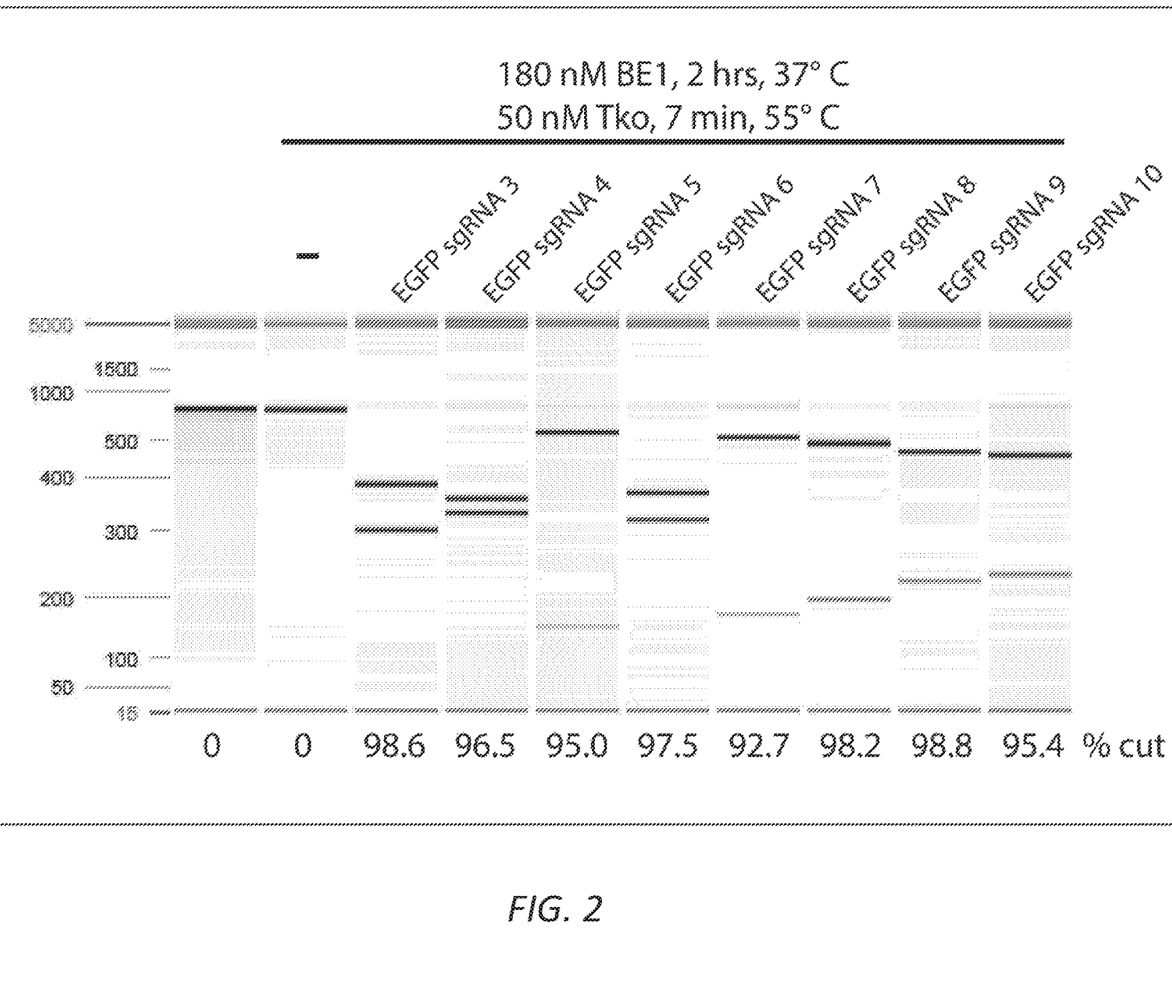
FIG. 2. Capillary electrophoresis data from an experiment demonstrating the specificity of TkoEndoMS' endonuclease activity for G:U DNA mismatches in vitro.

Example 1. TkoEndoMS Recognizes G:U Mismatches Resulting from a BE Deamination Event TkoEndoMS, a protein derived from *Thermococcus kodakarensis*, has previously been shown to recognize G:T mismatches[7]. A capillary electrophoresis experiment was performed to demonstrate the specificity of TkoEndoMS' endonuclease activity for G:U DNA mismatches in vitro. An 800 base pair PCR amplicon was incubated with purified BE protein and a variable sgRNA for two hours to induce site-specific deamination. After purification, the deaminated PCR amplicon was incubated with purified TkoEndoMS protein for 7 minutes to induce double strand breaks at G:U mismatches. The DNA was then separated by size by capillary electrophoresis and imaged. As shown in FIG. 2, TkoEndoMS efficiently recognized G:U mismatches resulting from a BE deamination event.

TkoEndoMS Sequence with N-Terminal Hexahistidine Tag for Protein Purification (SEQ ID NO: 1)
MGSSHHHHHHMSKDKVTVITSPSTEELVSLVNSALLEEAMLTIFARCKVHY

DGRAKSELGSGDRVIIVKPDGSFLIHQSKKREPVNWQPPGSRVRLELRENP

VLVSIRRKPRETLEVELEEVYMVSVFRAEDYEELALTGSEAEMAELIFENP

EVIEPGFKPLFREKAIGTGIVDVLGRDSDGNIVVLELKRRRAELHAVRQLK

SYVEILREEYGDKVRGILVAPSLTSGAKRLLEKEGLEFRKLEPPKRDSKKK

GRQKTLF

REFERENCES

1. Komor, Alexis C., Yongjoo B. Kim, Michael S. Packer, John A. Zuris, and David R. Liu. "Programmable Editing of a Target Base in Genomic DNA without Double-stranded DNA Cleavage." *Nature* 533.7603 (2016): 420-24.

2. Yang, Luhan, Adrian W. Briggs, Wei Leong Chew, Prashant Mali, Marc Guell, John Aach, Daniel Bryan Goodman, David Cox, Yinan Kan, Emal Lesha, Venkataramanan Soundararajan, Feng Zhang, and George Church. "Engineering and Optimising Deaminase Fusions for Genome Editing." *Nature Communications* 7 (2016): 13330.

3. Tsai, Shengdar Q., Zongli Zheng, Nhu T. Nguyen, Matthew Liebers, Ved V. Topkar, Vishal Thapar, Nicolas Wyvekens, Cyd Khayter, A. John Iafrate, Long P. Le, Martin J. Aryee, and J. Keith Joung. "GUIDE-seq Enables Genome-wide Profiling of Off-target Cleavage by CRISPR-Cas Nucleases." *Nature Biotechnology* 33.2 (2014): 187-97.

4. Wu, Xuebing, David A. Scott, Andrea J. Kriz, Anthony C. Chiu, Patrick D. Hsu, Daniel B. Dadon, Albert W. Cheng, Alexandro E. Trevino, Silvana Konermann, Sidi Chen, Rudolf Jaenisch, Feng Zhang, and Phillip A. Sharp. "Genome-wide Binding of the CRISPR Endonuclease Cas9 in Mammalian Cells." *Nature Biotechnology* 32.7 (2014): 670-76.

5. Kim, Daesik, Kayeong Lim, Sang-Tae Kim, Sun-Heui Yoon, Kyoungmi Kim, Seuk-Min Ryu, and Jin-Soo Kim. "Genome-wide Target Specificities of CRISPR RNA-guided Programmable Deaminases." *Nature Biotechnology* (2017).

6. Tsai, Shengdar Q., et al. "CIRCLE-seq: a highly sensitive in vitro screen for genome-wide CRISPR-Cas9 nuclease off-targets." *Nature Methods* (2017).

7. Ishino, Sonoko, et al. "Identification of a mismatch-specific endonuclease in hyperthermophilic Archaea." *Nucleic acids research* (2016): gkw153.

8. Suspene, Rodolphe, et al. "Recovery of APOBEC3-edited human immunodeficiency virus G→A hypermutants by differential DNA denaturation PCR." *Journal of general virology* 86.1 (2005): 125-129.

9. Aynaud, Marie-Ming, et al. "Human Tribbles 3 protects nuclear DNA from cytidine deamination by APOBEC3A." *Journal of Biological Chemistry* 287.46 (2012): 39182-39192.

10. Shinohara, Masanobu, et al. "APOBEC3B can impair genomic stability by inducing base substitutions in genomic DNA in human cells." *Scientific reports* 2 (2012): 806.

11. Suspene, Rodolphe, et al. "Extensive editing of both hepatitis B virus DNA strands by APOBEC3 cytidine deaminases in vitro and in vivo." *Proceedings of the National Academy of Sciences of the United States of America* 102.23 (2005): 8321-8326.

12. Holtz, Colleen M., Holly A. Sadler, and Louis M. Mansky. "APOBEC3G cytosine deamination hotspots are defined by both sequence context and single-stranded DNA secondary structure." *Nucleic acids research* (2013): gkt246.

13. Rebhandl, Stefan, Michael Huemer, Richard Greil, and Roland Geisberger. "AID/APOBEC Deaminases and Cancer." *Oncoscience* 2 (2015): 320.

14. Suspene, R., V. Caval, M. Henry, M. S. Bouzidi, S. Wain-Hobson, and J-P Vartanian. "Erroneous Identification of APOBEC3-edited Chromosomal DNA in Cancer Genomics." *British Journal of Cancer* 110.10 (2014): 2615-622. 15. Fu, Y., Sander, J. D., Reyon, D., Cascio, V. M. & Joung, J. K. Improving CRISPR-Cas nuclease specificity using truncated guide RNAs. *Nature Biotechnology*. 32, 279-284 (2014).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of detecting deaminated sites in substrate DNA, the method comprising:
providing a sample comprising substrate DNA;
deaminating the substrate DNA using a base editing fusion protein comprising a deaminase domain and a DNA binding domain;
contacting the deaminated substrate with Endonuclease MS from *Thermococcus kodakarensis* (TkoEndoMS) to induce double strand breaks (DSBs) at deamination sites in the substrate DNA to produce DNA fragments with single-stranded, five-base pair overhanging ends;
treating the DNA fragments with uracil DNA glycosylase and endonuclease VIII;
end-repairing and/or A-tailing the ends of the DNA fragments;
ligating an adapter oligonucleotide to the ends; and
sequencing the DNA fragments.

2. The method of claim 1, wherein the substrate DNA is genomic DNA (gDNA).

3. The method of claim 1, wherein the adapter oligonucleotide comprises a single deoxyuridine.

4. The method of claim 1, wherein sequencing the DNA fragments comprises determining a sequence of at least 10 nucleotides at the ends of the DNA fragments.

5. The method of claim 1, wherein the base editing fusion protein is selected from the group consisting of a zinc-finger domain; a transcription-activator-like effector domain; or a catalytically-inactive Cas9 or Cpf1, with a selected guide RNA.

6. The method of claim 1, wherein the adapter oligonucleotide comprises sequences for use in high throughput sequencing.

7. The method of claim 1, wherein the substrate DNA is synthesized DNA.

8. The method of claim 1, wherein the base editing fusion protein is selected from the group consisting of a zinc-finger domain; a transcription-activator-like effector domain; or a catalytically-inactive Cas9 or Cpf1, with a selected guide RNA, and wherein the substrate DNA is genomic DNA.

9. The method of claim 8, wherein the base editing fusion protein is a catalytically-inactive Cas9 or Cpf1, with a selected guide RNA.

10. The method of claim 1, wherein the base editing fusion protein is selected from the group consisting of a zinc-finger domain; a transcription-activator-like effector domain; or a catalytically-inactive Cas9 or Cpf1, with a selected guide RNA, and wherein the substrate DNA is synthesized DNA.

11. The method of claim 10, wherein the base editing fusion protein is a catalytically-inactive Cas9 or Cpf1, with a selected guide RNA.

* * * * *

SEQUENCE LISTING

<160> NUMBER OF SEQ ID NOS: 1

<210> SEQ ID NO 1
<211> LENGTH: 262
<212> TYPE: PRT
<213> ORGANISM: Thermococcus kodakarensis

<400> SEQUENCE: 1

Met Gly Ser Ser His His His His His His Met Ser Lys Asp Lys Val
1               5                   10                  15

Thr Val Ile Thr Ser Pro Ser Thr Glu Glu Leu Val Ser Leu Val Asn
            20                  25                  30

Ser Ala Leu Leu Glu Glu Ala Met Leu Thr Ile Phe Ala Arg Cys Lys
        35                  40                  45

Val His Tyr Asp Gly Arg Ala Lys Ser Glu Leu Gly Ser Gly Asp Arg
    50                  55                  60

Val Ile Ile Val Lys Pro Asp Gly Ser Phe Leu Ile His Gln Ser Lys
65                  70                  75                  80

Lys Arg Glu Pro Val Asn Trp Gln Pro Pro Gly Ser Arg Val Arg Leu
                85                  90                  95

Glu Leu Arg Glu Asn Pro Val Leu Val Ser Ile Arg Arg Lys Pro Arg
            100                 105                 110

Glu Thr Leu Glu Val Glu Leu Glu Val Tyr Met Val Ser Val Phe
            115                 120                 125

Arg Ala Glu Asp Tyr Glu Glu Leu Ala Leu Thr Gly Ser Glu Ala Glu
        130                 135                 140

Met Ala Glu Leu Ile Phe Glu Asn Pro Glu Val Ile Glu Pro Gly Phe
145                 150                 155                 160

Lys Pro Leu Phe Arg Glu Lys Ala Ile Gly Thr Gly Ile Val Asp Val
                165                 170                 175

Leu Gly Arg Asp Ser Asp Gly Asn Ile Val Val Leu Glu Leu Lys Arg
            180                 185                 190

Arg Arg Ala Glu Leu His Ala Val Arg Gln Leu Lys Ser Tyr Val Glu
        195                 200                 205

Ile Leu Arg Glu Glu Tyr Gly Asp Lys Val Arg Gly Ile Leu Val Ala
    210                 215                 220

Pro Ser Leu Thr Ser Gly Ala Lys Arg Leu Leu Glu Lys Glu Gly Leu
225                 230                 235                 240

Glu Phe Arg Lys Leu Glu Pro Pro Lys Arg Asp Ser Lys Lys Lys Gly
                245                 250                 255

Arg Gln Lys Thr Leu Phe
            260